US00PP35982P2

(12) United States Plant Patent
Koot et al.

(10) Patent No.: US PP35,982 P2
(45) Date of Patent: Jul. 9, 2024

(54) DIPLADENIA PLANT NAMED 'DODIPCHO'

(50) Latin Name: *Mandevilla sanderi*
Varietal Denomination: Dodipcho

(71) Applicant: DUMMEN GROUP B.V., De Lier (NL)

(72) Inventors: Arjan Koot, Oeffelt (NL); Josep Escriba, Puerto Lumbreras Murcia (ES)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 18/384,697

(22) Filed: Oct. 27, 2023

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./226, 232
See application file for complete search history.

(56) References Cited

U.S. PATENT DOCUMENTS

PP24,075 P2 * 12/2013 Lannes ..... A01H 5/02
Plt./226

* cited by examiner

*Primary Examiner* — Karen M Redden
(74) *Attorney, Agent, or Firm* — C. Anne Whealy

(57) ABSTRACT

A new and distinct cultivar of *Dipladenia* plant named 'Dodipcho', characterized by its broadly upright plant habit; moderately vigorous growth habit and moderate growth rate; freely branching habit; dense and bushy appearance; glossy dark green-colored leaves; freely flowering habit; deep red-colored flowers with orange-colored throats; and good garden performance.

2 Drawing Sheets

Figure 1:
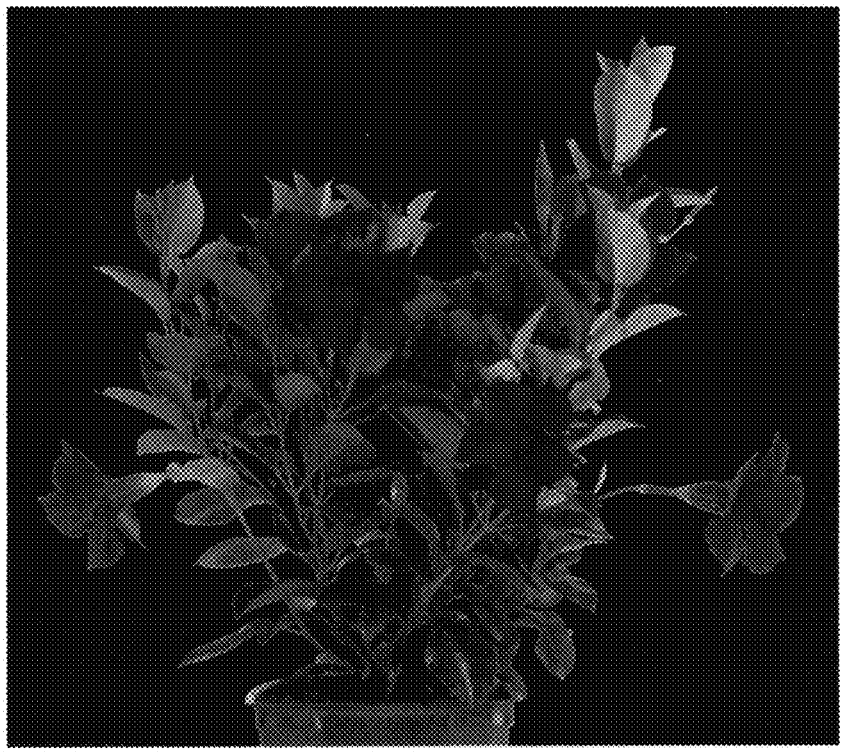

Botanical designation: *Mandevilla sanderi.*
Cultivar denomination: 'DODIPCHO'.

BACKGROUND OF THE INVENTION

The present invention relates to a new and distinct cultivar of *Dipladenia* plant, commonly referred to as *Mandevilla*, botanically known as *Mandevilla sanderi* and hereinafter referred to by the name 'Dodipcho'.

The new *Dipladenia* plant is a product of a planned breeding program conducted by the Inventors in Rheinberg, Germany and Puerto Lumbreras, Murcia, Spain. The objective of the breeding program is to create new freely branching *Dipladenia* plants that flower freely and have attractive flower colors.

The new *Dipladenia* plant originated from a self-pollination conducted by the Inventors in Rheinberg, Germany in September, 2020 of a proprietary breeding selection of *Mandevilla sanderi* identified as code number MM07-001106-068, not patented. The new *Dipladenia* plant was discovered and selected by the Inventors as a single flowering plant from within the progeny of the stated self-pollination in a controlled greenhouse environment in Puerto Lumbreras, Murcia, Spain in September, 2021.

Asexual reproduction of the new *Dipladenia* plant by vegetative cuttings in a controlled greenhouse environment in Puerto Lumbreras, Murcia, Spain since November, 2021 has shown that the unique features of this new *Dipladenia* plant are stable and reproduced true to type in successive generations.

SUMMARY OF THE INVENTION

Plants of the new *Dipladenia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dodipcho'. These characteristics in combination distinguish 'Dodipcho' as a new and distinct *Dipladenia* plant:

1. Broadly upright plant habit.
2. Moderately vigorous growth habit and moderate growth rate.
3. Freely branching habit; dense and bushy appearance.
4. Glossy dark green-colored leaves.
5. Freely flowering habit.
6. Deep red-colored flowers with orange-colored throats.
7. Good garden performance.

Plants of the new *Dipladenia* can be compared to plants of the parent selection. Plants of the new *Dipladenia* differ primarily from plants of the parent selection in the following characteristics:

1. Plants of the new *Dipladenia* are more compact than plants of the parent selection.
2. Plants of the new *Dipladenia* have shorter internodes than plants of the parent selection.
3. Plants of the new *Dipladenia* have smaller leaves than plants of the parent selection.
4. Flower petals of plants of the new *Dipladenia* are flatter than flower petals of the parent selection.
5. Flowers of plants of the new *Dipladenia* are darker red in color than flowers of plants of the parent selection.

Plants of the new *Dipladenia* can also be compared to plants of *Mandevilla sanderi* 'Laniowa', disclosed in U.S. Plant Pat. No. 24,075. In side-by-side comparisons, plants of the new *Dipladenia* differ primarily from plants 'Laniowa' in the following characteristics:

1. Leaves of plants of the new *Dipladenia* are smaller and more rounded than leaves of plants of 'Laniowa'.
2. Plants of the new *Dipladenia* are more freely flowering than plants of 'Laniowa'.
3. Plants of the new *Dipladenia* have smaller flowers than plants of 'Laniowa'.
4. Flowers of plants of the new *Dipladenia* are darker red in color than flowers of plants of 'Laniowa'.

BRIEF DESCRIPTION OF THE PHOTOGRAPHS

The accompanying colored photographs illustrate the overall appearance of the new *Dipladenia* plant showing the colors as true as it is reasonably possible to obtain in colored reproductions of this type. Colors in the photographs may differ slightly from the color values cited in the detailed botanical description which accurately describe the actual colors of the new *Dipladenia* plant.

The photograph on the first sheet (FIG. 1) is a side perspective view of a typical flowering plant of 'Dodipcho' grown in a container.

Figure 2:
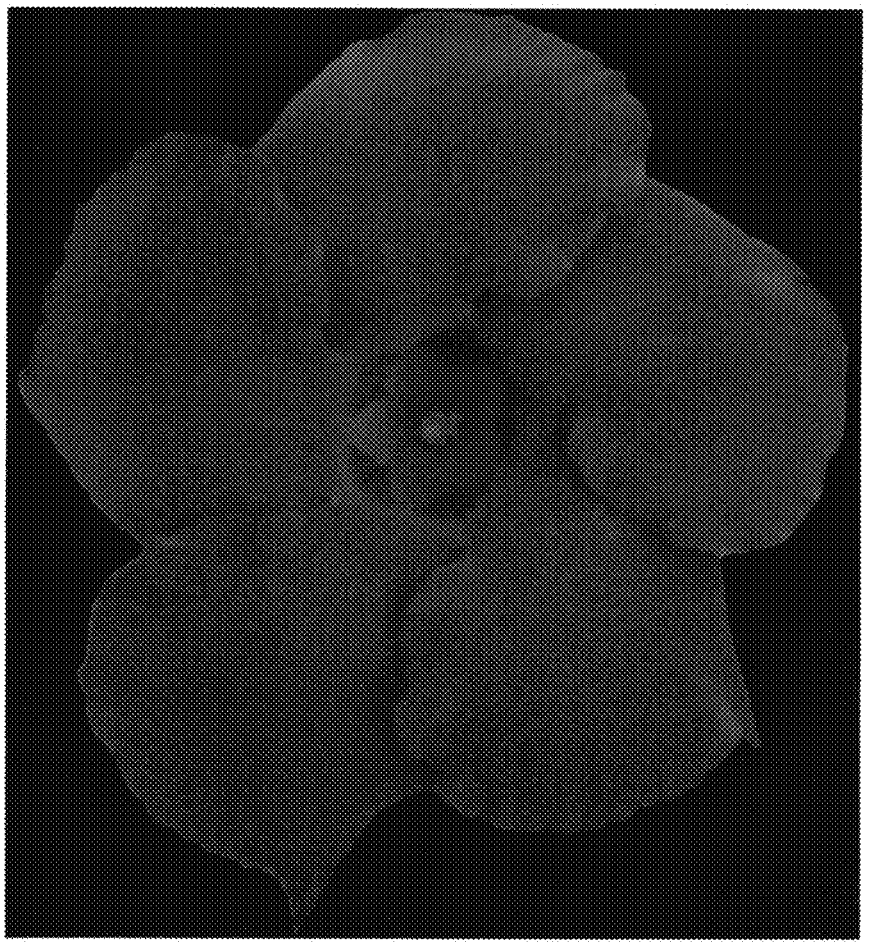

The photograph on the second sheet (FIG. 2) is a close-up view of a typical flower of 'Dodipcho'.

DETAILED BOTANICAL DESCRIPTION

The aforementioned photographs and following observations, measurements and values describe plants grown during the spring in 17-cm containers in a polyethylene-covered greenhouse in Puerto Lumbreras, Murcia, Spain and under cultural practices typical of commercial *Dipladenia* production. During the production of the plants, day temperatures averaged 21.9C, night temperatures averaged 11.25C and light levels averaged 650 watts/m2/h. Plants were two years old when the photographs and description were taken. In the following description, color references are made to The Royal Horticultural Society Colour Chart, 1986 Edition, except where general terms of ordinary dictionary significance are used.

Botanical classification: *Mandevilla sanderi* 'Dodipcho'.

Parentage:

*Female, or seed, parent.*—Proprietary breeding selection of *Mandevilla sanderi* identified as code number MM07-001106-068, not patented.

*Male, or pollen, parent.*—Proprietary breeding selection of *Mandevilla sanderi* identified as code number MM07-001106-068, not patented.

Propagation:

*Type.*—By vegetative cuttings.

*Time to initiate roots, summer.*—About three weeks at temperatures about 30C.

*Time to initiate roots, winter.*—About three weeks at temperatures about 20C.

*Time to produce a rooted young plant, summer.*—About 42 days at temperatures about 30C.

*Time to produce a rooted young plant, winter.*—About 50 days at temperatures about 20C.

*Root description.*—Thick, fleshy; typically white and brown in color, actual color of the roots is dependent on substrate composition, water quality, fertilizers, substrate temperature and physiological age of roots.

*Rooting habit.*—Moderately freely branching; medium density.

Plant description:

*Plant and growth habit.*—Broadly upright plant habit; moderately vigorous growth habit and moderate growth rate; freely branching habit, dense and bushy appearance.

*Plant height.*—About 70 cm.

*Plant diameter (spread).*—About 50 cm.

*Lateral branch description.*—Branching habit: Freely branching habit, typically about three primary lateral branches each with about four secondary lateral branches per plant; pinching enhances lateral branch development. Length: About 50 cm. Diameter: About 1.5 mm. Internode length: About 4.1 cm. Strength: Moderately strong. Texture and luster: Smooth, glabrous; semi-glossy; becoming woody with development. Color, developing: Close to 166A. Color, developed: Close to 144A; at the internodes, close to 152D; when woody, close to 165A.

Leaf description:

*Arrangement.*—Opposite, simple.

*Length.*—About 7 cm.

*Width.*—About 4 cm.

*Shape.*—Elliptical.

*Apex.*—Apiculate.

*Base.*—Rounded.

*Margin.*—Entire.

*Texture and luster, upper and lower surfaces.*—Smooth, glabrous; glossy.

*Venation pattern.*—Pinnate.

*Color.*—Developing leaves, upper surface: Close to 144A. Developing leaves, lower surface: Close to 147B. Full expanded leaves, upper surface: Close to 147A; venation, close to 147A. Fully expanded leaves, lower surface: Close to 147B; venation, close to 144D.

*Petioles.*—Length: About 9 mm. Diameter: About 1.5 mm. Strength: Strong. Texture and luster, upper and lower surfaces: Smooth, glabrous; glossy. Color, upper surface: Close to 145A. Color, lower surface: Close to 145B.

Flower description:

*Flower type and flowering habit.*—Star-shaped salver-form flowers arranged in terminal and axillary racemes; flowers face mostly upright to outwardly; freely flowering habit with about three or four flowers per inflorescence and about 49 flower buds and open flowers developing per plant during the flowering season.

*Natural flowering season.*—Plants flower continuously from spring into the autumn in Spain; plants begin flowering about 20 weeks after propagation (dependent on light level).

*Flower longevity on the plant.*—Individual flowers last about four to six days; flowers persistent.

*Fragrance.*—None detected.

*Inflorescence height.*—About 12 cm.

*Inflorescence diameter.*—About 12 cm.

*Flower buds.*—Length: About 6.3 cm. Diameter: About 1 cm. Shape: Elongated, spindle-shaped. Texture and luster: Smooth, glabrous; glossy. Color: Close to 59A.

*Flowers.*—Appearance: Flared trumpet, corolla fused and five-parted. Diameter: About 6.5 cm by 6.5 cm.

Depth (length): About 4 cm. Throat diameter: About 1.6 cm. Tube length: About 3.5 cm. Tube diameter: About 5 mm.

*Corolla.*—Quantity and arrangement: Five petals arranged in a single whorl; lower portion of the petals are fused into a funnelform tube. Petal length, free lobes: About 3.4 cm. Petal width, free lobes: About 3.5 cm. Petal shape and appearance: Roughly spatulate. Petal apex: Apiculate. Petal margin: Entire; moderately undulate. Petal texture and luster, upper and lower surfaces: Smooth, glabrous; matte. Throat texture: Smooth, glabrous. Tube texture: Smooth, glabrous. Color: Petal, when opening and fully opened, upper surface: Close to 60A; venation, close to 60B; color becoming closer to 57C with subsequent development. Petal, when opening and fully opened, lower surface: Close to 60B; venation, close to 60B; color becoming closer to 57D with subsequent development. Throat: Close to 24A; venation, close to 25A. Tube: Close to 144C; venation, close to 144C.

*Sepals.*—Quantity and arrangement: Five sepals arranged in a single whorl. Length: About 9 mm. Width: About 3 mm. Shape: Ligulate. Apex: Acuminate. Base: Acute. Margin: Entire. Texture and luster, upper and lower surfaces: Smooth, glabrous; semi-glossy. Color: When developing, upper and lower surfaces: Close to 144D. Fully opened, upper and lower surfaces: Close to 144D.

*Peduncles.*—Length: About 1.2 cm. Diameter: About 1.5 mm. Strength: Strong. Aspect: About 45 degrees from lateral branch axis. Texture and luster: Smooth, glabrous; matte. Color: Close to 154C.

*Pedicels.*—Length: About 1.5 cm. Diameter: About 1 mm. Strength: Strong. Aspect: About 45 degrees from peduncle axis. Texture and luster: Smooth, glabrous; matte. Color: Close to 144A.

*Reproductive organs.*—Stamens: Quantity and arrangement: Typically five; basifixed; anthers connivent. Filament length: About 2 mm. Filament color: Close to 8B. Anther size: About 4 mm by 9 mm. Anther shape: Narrowly oblong, elongated. Anther color: Close to 3C. Pollen amount: Moderate. Pollen color: Close to 3C. Pistils: Quantity: Typically one. Pistil length: About 5 mm. Style length: About 2.3 mm. Style color: Close to 1D. Stigma diameter: About 1.8 mm. Stigma shape: Star-shaped. Stigma color: Close to 145A. Ovary color: Close to 1D.

*Seeds and fruits.*—To date, seed and fruit production have not been observed on plants of the new *Dipladenia.*

Pathogen & pest resistance: To date, plants of the new *Dipladenia* have not been noted to be resistant to pathogens and pests common to *Dipladenia* plants.

Garden performance: Plants of the new *Dipladenia* have been observed to have good garden performance.

It is claimed:

1. A new and distinct *Dipladenia* plant named 'Dodipcho' as illustrated and described.

* * * * *